United States Patent [19]

Herman et al.

[11] Patent Number: 5,495,747
[45] Date of Patent: Mar. 5, 1996

[54] DEVICE FOR DETECTING GASES FOR USE IN DIFFUSION AND FORCED FLOW MODES

[75] Inventors: Roberta A. Herman, Cranberry Township; Daniel E. Bruce, Murrysville; Alan A. Schneider, Wexford; Stephen E. Long, Murrysville, all of Pa.

[73] Assignee: Mine Safety Appliances Company, Pittsburgh, Pa.

[21] Appl. No.: 315,709

[22] Filed: Sep. 30, 1994

[51] Int. Cl.$^6$ .......................... G01N 27/16; G01N 27/00; G08B 17/10
[52] U.S. Cl. .......................... 73/23.21; 73/25.01; 73/23.2
[58] Field of Search .......................... 73/23.2, 23.31, 73/23.21, 25.01; 204/427, 153.18; 338/34, 22 RO

[56] References Cited

U.S. PATENT DOCUMENTS

| | | | |
|---|---|---|---|
| 3,607,084 | 9/1971 | Mackey et al. | 23/232 |
| 4,063,898 | 12/1977 | Fisher | 23/254 |
| 4,184,934 | 1/1980 | Bode et al. | 204/195 S |
| 4,305,724 | 12/1981 | Micko | 23/232 E |
| 4,477,403 | 10/1984 | Pust | 264/104 |
| 4,703,646 | 11/1987 | Müller et al. | 73/23 |
| 4,818,977 | 4/1989 | Alexander | 340/633 |
| 4,869,094 | 9/1989 | Kozuka et al. | 73/2.6 |
| 5,055,269 | 10/1991 | Palumbo et al. | 422/96 |

*Primary Examiner*—Hezron E. Williams
*Assistant Examiner*—J. David Wiggins
*Attorney, Agent, or Firm*—Henry E. Bartony, Jr.; James G. Uber

[57] ABSTRACT

A gas detection device is provided comprising an exterior housing in which an active pelement and a compensating pelement are disposed. The gas detection device further comprises a porous frit seated within a distal end of the exterior housing to separate the active pelement and the compensating pelement from the surrounding environment. The porous frit is adapted to prevent flashback into the surrounding environment while allowing movement of environmental gas through the porous frit to contact the active pelement and the compensating pelement. The gas detection device further comprises a flow guide for directing flow of environmental gas into the gas detection device disposed adjacent the exterior side of the porous frit. The flow guide comprises an inlet port through which a forced flow of environmental gas is pumped to pass through the porous frit and into the exterior housing in a direction generally parallel to the axis of the exterior housing. The flow guide also comprises an outlet port through which gas may exit the exterior housing. A gas detection device is also provided in which the electrical resistance of the compensating pelement is measured to determine concentration of combustible gas at combustible gas concentration levels above a predetermined concentration level set equal to the LEL (Lower Explosive Limit). The gas detection comprises a circuit for reducing current passing through the active pelement when the gas detection device is being used above the predetermined concentration level.

13 Claims, 16 Drawing Sheets

DEVICE FOR DETECTING GASES FOR USE IN DIFFUSION AND FORCED FLOW MODES

FIELD OF THE INVENTION

The present invention relates to a device for the detection of gases, and especially to a device for the detection of combustible gases which may operate either in a diffusion mode or in a forced flow mode.

BACKGROUND OF THE INVENTION

Combustible (flammable) gas detectors have been in use for many years for the prevention of explosive accidents. Conventional gas detectors operate by catalytic oxidation of combustible gases. Such gas detectors comprise a platinum wire coil encased in a refractory (for example, alumina) bead, the surface area of which is covered with a catalyst. This encased platinum coil is commonly referred to as a pelement or a pellister. A detailed discussion of pelement and catalytic combustible gas detectors comprising such pelement is found in Mosely, P. T. and Tofield, B. C., ed., *Solid State Gas Sensors*, Adams Hilger Press, Bristol, England (1987), the disclosure of which is incorporated herein by reference.

In general, the pelement operates as a miniature calorimeter used to measure the energy liberated upon oxidation of a combustible gas. The platinum element serves two purposes within the pelement: (1) heating the bead electrically to its operating temperature (typically approximately 500° C. and (2) detecting changes in temperature produced by oxidation of the combustible gas.

The increase in temperature is measured in terms of the variation in resistance of the platinum element (with temperature variation) relative to a reference resistance. The two resistances are part of a Wheatstone bridge circuit. The voltage developed across the circuit when a combustible gas is present provides a measure of the concentration of the combustible gas. The reference resistor generally comprises a compensating, nonactive pelement matched as closely as possible with the pelement carrying the catalyst.

Typically, the active pelement and the compensating pelement are deployed within an explosion-proof housing and are separated from the surrounding environment by a porous metal frit. The porous metal frit allows ambient gases to pass therethrough but prevents the "flashback" of flames into the surrounding environment. An example of a modular gas detector cell incorporating such a frit is illustrated in FIG. 1A.

Combustible gas detectors may act in one of two modes: (1) diffusion of gas into the pelements and (2) forced flow of gas into the vicinity of the pelements. In the case of a gas detector operating in the diffusion mode, a gas detector cell (such as illustrated in FIG. 1A) is placed into an environment in which combustible gasses are to be detected. The gas detector cell is typically encased within the gas monitoring unit, not shown in FIG. 1A. The gases comprising the surrounding environment diffuse through the frit to contact the active and compensating pelements within the monitoring unit.

The amount of time required for environmental gases to diffuse to the frit, through the frit and to the pelements creates a delay in the response time of the monitoring unit. In certain uses, such a delay in determining the combustible gas content of the environment is undesirable. In such cases, environmental gases may be forced via pumping to the vicinity of the gas detector cell to reduce the response time.

The forced flow of gas to a detector housing is often required in remote sampling, for example, in which a probe is placed in fluid connection via tubing to the gas detector. An example of such a detector is the PASSPORT® detector available from Mine Safety Appliances Company of Pittsburgh, Pa. In that detector, environmental gases are pumped into a plenum located above a frit of a modular gas detector cell as illustrated in FIG. 1A. These gases then diffuse through the frit to contact the pelements.

Another example of a detector operating in a forced flow mode is the GASURVEYOR device available from GMI of Renfrew, Scotland. The gas detector cell used in that device is illustrated in FIG. 1B. As illustrated, environmental gases are pumped through the detector cell which is equipped with frits at the entrance and exit of the housing to prevent flashback. Environmental gases flow over and into two wells in which the active pelement and the compensating pelement are seated. In the case of the GASURVEYOR device, the flow rate is maintained sufficiently high to create turbulent flow through the detector cell such that a component of the flow enters the wells surrounding the pelements. Absent turbulent flow, environmental gases would diffuse into the wells surrounding the pelements from the forced flow (oriented perpendicular to such wells), but the response time would reflect the delay associated with such diffusion.

Stricter response time requirements for gas detectors continue to be imposed by consumers of gas detection systems. Therefore, manufacturers of gas detectors continue their attempt to minimize such response times while maintaining competitive pricing. It is thus very desirable to develop a "flow-through" or forced-flow gas detector with improved response time and low manufacturing costs.

SUMMARY OF THE INVENTION

Accordingly, the present invention provides a gas detection device providing a response time exceeding the response times achievable with prior gas detection devices. Moreover, the present device can easily (and inexpensively) be manufactured by a simple retrofit to the design of presently available gas detection cells. Still further, the present gas detection device may be used in a forced-flow mode or a diffusion mode and at concentration levels of combustible gas ranging from PPM levels to 100% combustible gas.

In general, the present invention provides a gas detection cell comprising an exterior housing in which an active pelement and a compensating pelement are disposed. The gas detection device further comprises a porous frit seated within a distal end of the exterior housing to separate the active pelement and the compensating pelement from the surrounding environment. The porous frit is adapted to prevent flashback into the surrounding environment while allowing movement of environmental gas through the porous frit to contact the active pelement and the compensating pelement.

The porous frit thus has an interior side within the exterior housing and an exterior side outside the exterior housing. The gas detection device further comprises a flow guide for directing flow of environmental gas into the gas detection device disposed adjacent to and preferably in contact with the exterior side of the porous frit. The flow guide comprises an inlet port through which a forced flow of environmental gas is pumped to pass through the porous frit and into the exterior housing in a direction generally parallel to the axis of the exterior housing. The flow guide also comprises an outlet port through which gas may exit the gas detection device.

The flow guide preferably comprises a bypass passage for providing fluid connection between the inlet port and the environment. A portion of environmental gas pumped to the inlet port is thereby allowed to bypass the porous frit in a flow controlling function that never permits such portion of environmental gas to enter within the exterior housing. In this manner, relatively high flow rates of environmental gas may be maintained to the inlet port without overwhelming the active pelement. Preferably, the bypass passage comprises a channel providing fluid connection between the inlet port and the outlet port.

Additionally, by removing the forced flow from the present gas detection device (and preferably removing the flow guide) the present gas detection device is suited for operation in a diffusion mode similar to currently available detection cells designed for operation in a diffusion mode.

The present invention also provides a gas detection device comprising an active pelement, a compensating pelement and a circuit for measuring the electrical resistance of the compensating pelement, wherein the electrical resistance of the compensating pelement is used to determine the concentration of combustible gas, preferably at combustible gas concentration levels above a predetermined concentration level (for example, above 100% Lower Explosive Limit—LEL). Below the predetermined concentration level, the active pelement and the compensating pelement are utilized in a Wheatstone bridge circuit to determine combustible gas concentration.

Preferably, the gas detection device further comprises a circuit for reducing current passing through the active pelement when the gas detection device is being used above the predetermined concentration level, thereby reducing the temperature of the active pelement below that temperature at which substantial catalytic oxidation occurs. Preferably, the circuit for reducing current passing through the active pelement comprises a transistor in parallel electrical connection with the active pelement. The transistor is preferably adapted to be switchable between a high-conductivity state and a low-conductivity state, such that the transistor may be switched on (that is, into the high-conductivity state) when operating above the predetermined concentration level and off (that is, into the low-conductivity state) when operating below the predetermined concentration level.

DETAILED DESCRIPTION OF THE INVENTION

Figure 2A:
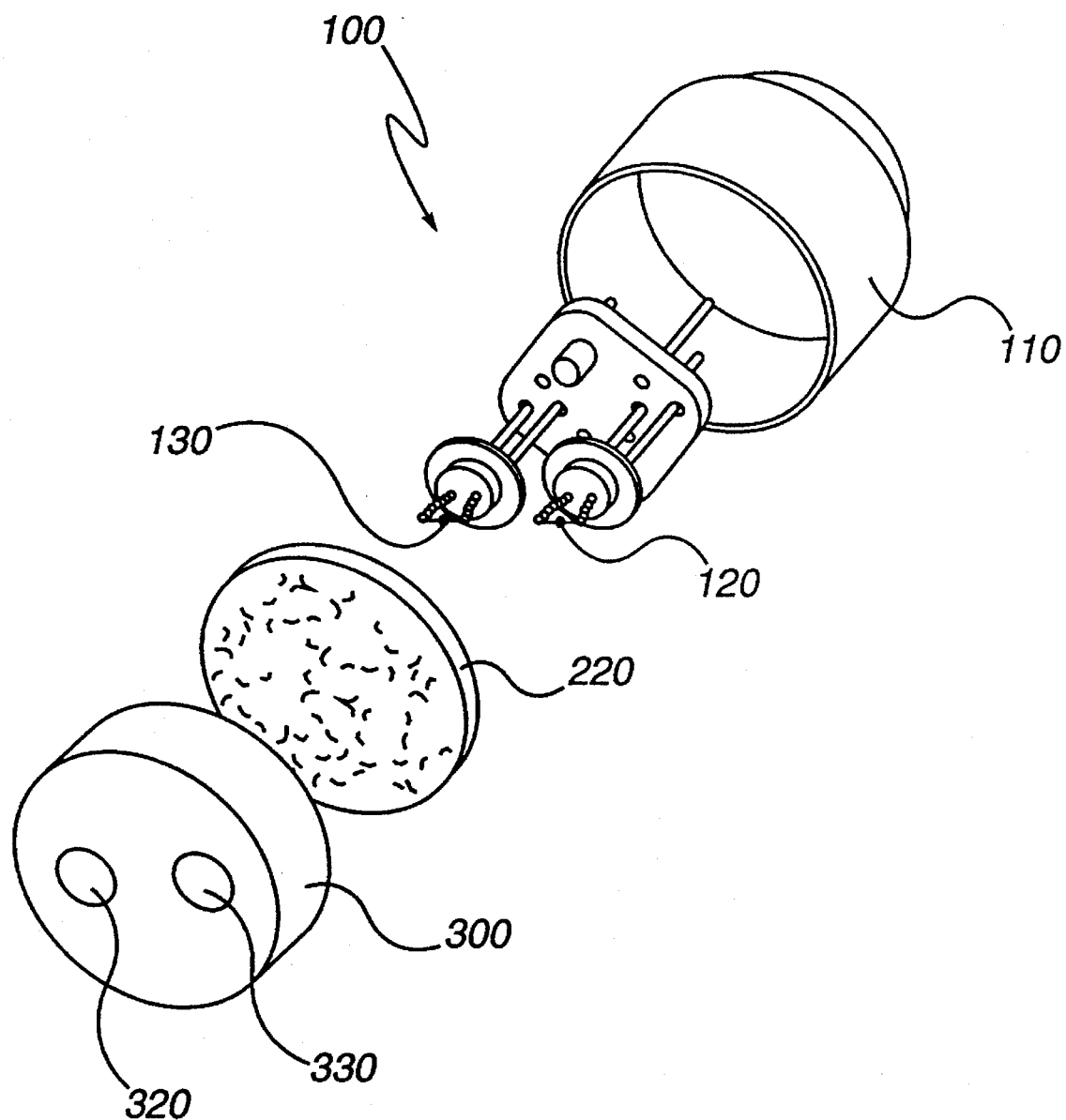
FIGS. 2A through 2C illustrate several embodiments of the present gas detection device.

Referring to FIG. 2A, the present gas detection device 100 comprises an external housing 110, within which are positioned an active pelement 120 and a compensating pelement 130 as known in the art.

A frit 220 (as known in the art) is placed over pelements 120 and 130 to prevent flashback. Frit 220 is preferably sized to fit securely within the upper perimeter of housing 110. A device such as a pump for providing a forced flow of environmental gases to gas detection device 100 is placed in fluid connection with a flow guide such as manifold 300 for directing the forced flow into gas detection device 100. Manifold 300 is positioned adjacent to and preferably in contact with frit 220 upon the side thereof opposite pelements 120 and 130. Manifold 300 comprises a flow inlet passage 320 therethrough. Flow inlet passage 320 is placed in fluid connection with a conduit such as tubing (not shown) through which environmental gases are pumped. Manifold 300 further comprises a flow outlet passage 330.

Environmental gases are forced through inlet passage 320 and into the space within exterior housing 110. The environmental gases contact pelements 120 and 130 and exit housing 110 via outlet passage 330. Unlike prior combustible gas detection devices, gas detection device 100 directs environmental gases to flow parallel to the axis of housing 110 and thus parallel to the orientation or seating of pelements 120 and 130 in housing 110, thereby optimizing the response time of gas detection device 100 for a given flow rate.

To minimize the response time of gas detection device 100, it is desirable to maximize the forced flow rate of the environmental gasses entering gas detection device 100 to ensure that the sample reaches pelements 120 and 130 as quickly as possible. Moreover, higher flow rates provide a greater signal from pelements 120 and 130 as measured using the Wheatstone bridge.

However, the a amount of active catalyst sites upon active pelement 120 is limited. For a given concentration of combustible gas within the environment there will exist a flow rate above which the active pelement will be overwhelmed (that is, all active sites will be utilized and an amount of unoxidized combustible gas will leave detection device 100). Therefore, as flow rate is increased, the signal provided from pelements 120 and 130 becomes "nonlinear" at a given concentration (that is, the signal does not accurately reflect actual gas concentration). Generally, the calculated gas concentration is found to be less than the actual gas concentration because not all of the combustible gas is being oxidized. There is, thus, a tradeoff between flow rate (and response time) and the accuracy of the signal.

To maximize the flow rate to gas detection device 100, gas detection device 100 preferably includes a flow limiter for reducing the total amount of gas to reach pelements 120 and 130 situated between manifold 300 and pelements 120 and 130. Preferably, the flow limiter comprises a semipermeable or porous medium. The flow limiter may comprise frit 220. Frits 220 of differing porosity are available from a number of manufacturers, including Mott Metallurgical Corp.

Figure 2B:
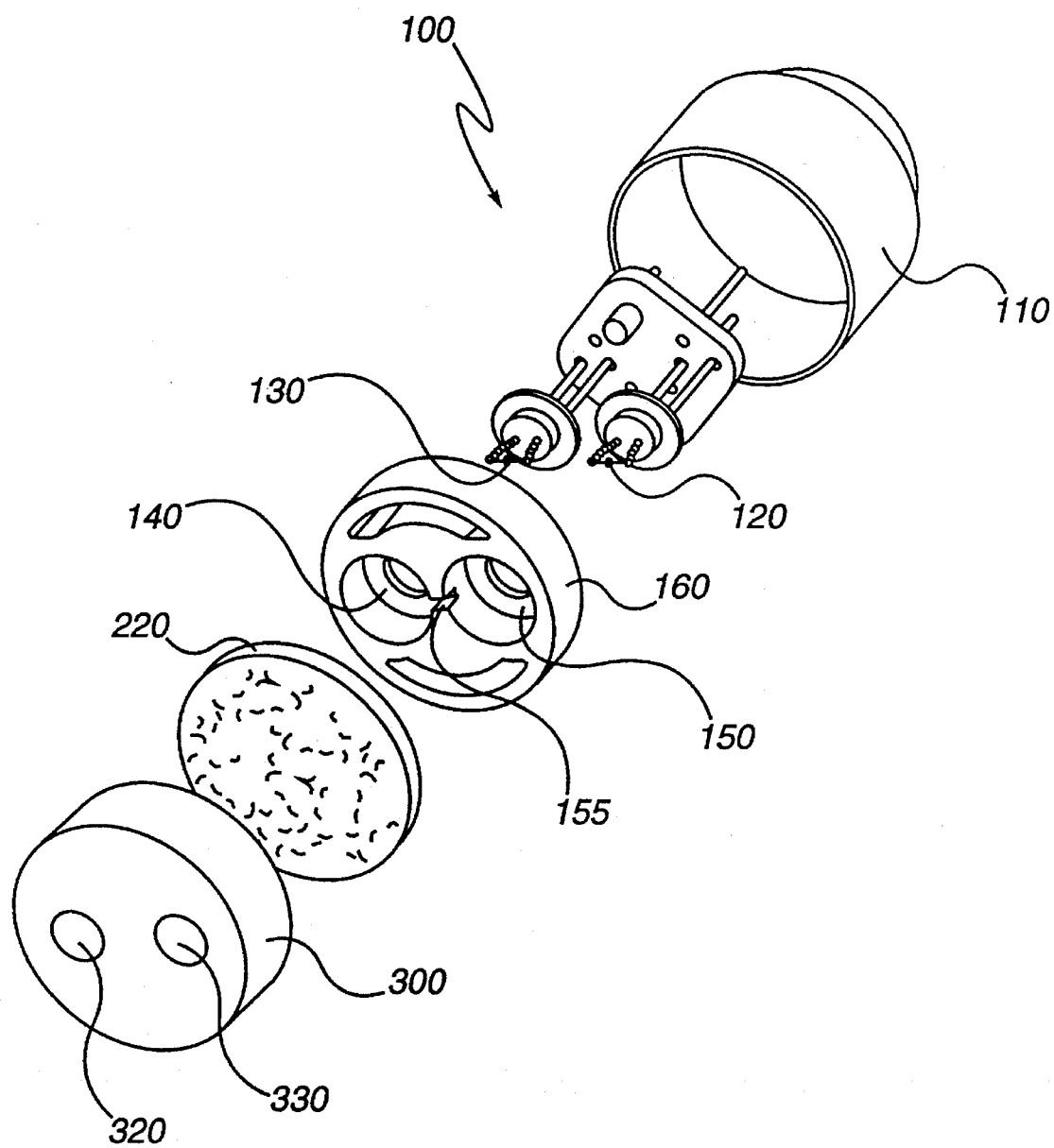
Figure 2C:
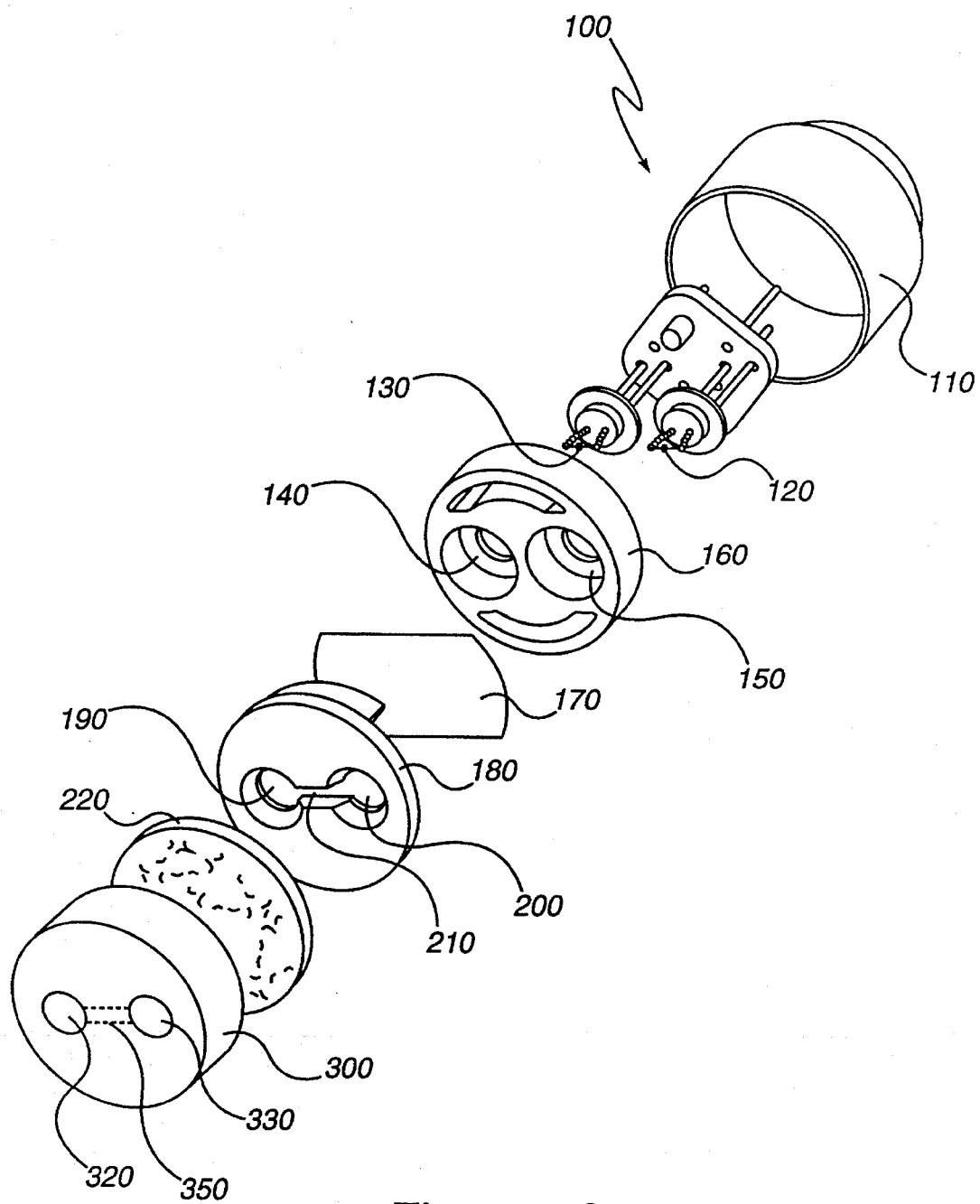
Figure 3:
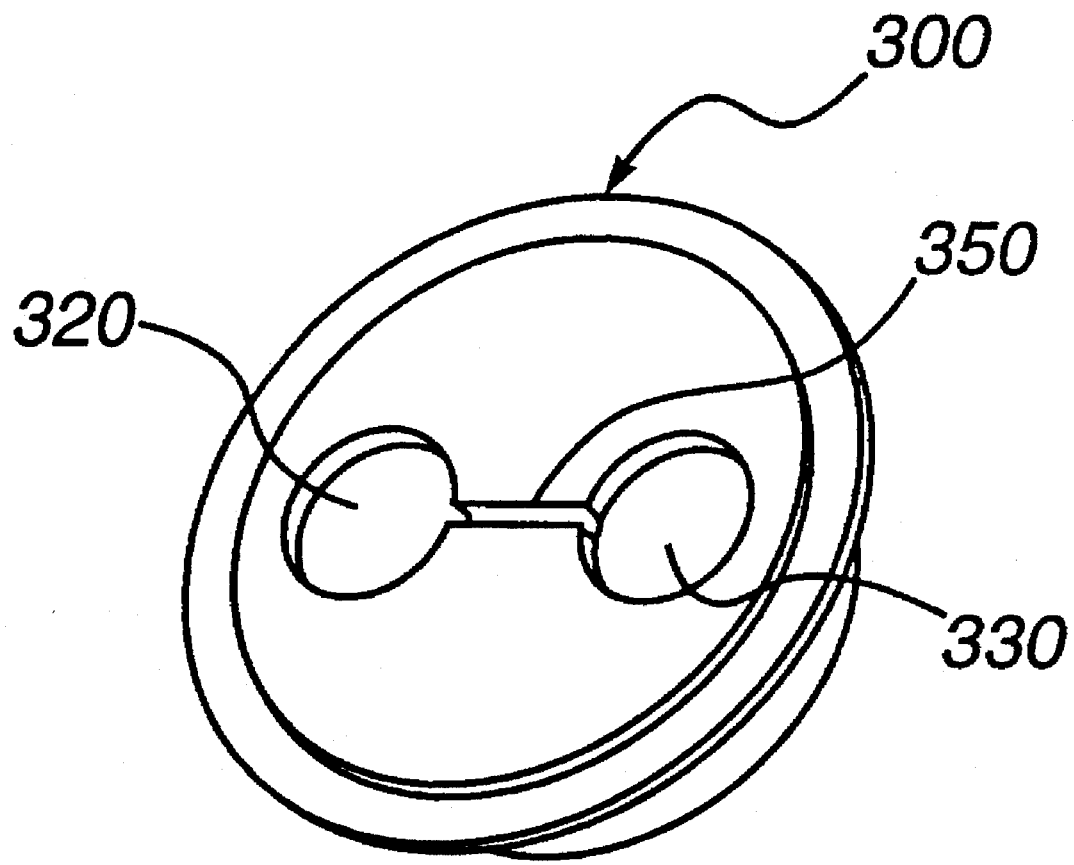
FIG. 3 illustrates an embodiment of a manifold for use in the gas detection device of FIGS. 2A through 2C.

Preferably, manifold 300 is provided with a bypass passage for providing fluid connection between inlet passage 320 and the surrounding environment. As illustrated in FIGS. 2C and 3, this bypass passage may comprise a bypass channel 350 for providing fluid connection between inlet passage 320 and outlet passage 330. Upon entrance into inlet passage 320, a forced flow of environmental gasses will encounter porous frit 220 which restricts the amount of gas allowed to enter gas detection device 100 to contact pelements 120 and 130. A portion of the forced flow of environmental gasses will, therefore, flow through bypass channel 350 and exit via outlet passage 330. In this manner, a relatively high forced flow rate may be maintained while limiting the amount of environmental gasses reaching pelements 120 and 130, thereby substantially maximizing response time while preventing overwhelming of active pelement 120 and the associated inaccuracy in gas detection.

Manifold 300 is best illustrated in FIG. 3. The provision of various manifolds 300 having bypass channels 350 of varying size or with no bypass channel 350 enables tuning of gas detection device 100 for optimal use in various flow rates and thereby for optimal use to detect the presence of gas in various concentration ranges.

As discussed above, by providing bypass channel 350, the forced flow rate can be maintained relatively high to provide a quick response time while minimizing the nonlinearity effects of such a high flow rate. Detection of gas concentrations at low concentration levels (for example is, at PPM levels) requires a relatively high forced flow rate to provide an adequate signal. Therefore, to detect gas at such levels, bypass of gas flow from passing through frit 220 is preferably minimized or eliminated. At higher concentrations, such as in the 0 to 100% LEL range, bypass is preferably increased to reduce nonlinearity. In this manner gas detection device 100 can operate effectively over a wide range of gas concentrations with only minimal adjustment.

Preferably, heat transfer between active pelement 120 and compensating pelement 130 is minimized to prevent a decrease in the signal provided from the bridge circuit. Preferably, compensating pelement 130 and active pelement 120 are thus seated, respectively, within filament wells 140 and 150 in an interior housing 160 disposed within exterior housing 110 (FIG. 2B). As shown in FIG. 2B, interior housing 160 preferably comprises a passage for providing fluid connection between filament wells 140 and 150 to ensure that environmental gasses forced into gas detection device 100 contact both active pelement 120 and compensating pelement 130. Preferably, the passage for providing fluid connection between filament wells 140 and 150 comprises a channel 155 in interior housing 160 connecting filament wells 140 and 150. Channel 155 is preferably located at a distal end of interior housing 160 opposite the location of pelements 120 and 130 to minimize heat transfer therebetween.

Because of the limited porosities of frits 300 commercially available and the expense involved in manufacturing such frits 300, the flow limiter for reducing the total amount of gas to reach pelements 120 and 130 preferably further comprises a porous medium in addition to frit 300. As illustrated in FIG. 2C, a porous film 170 is preferably disposed adjacent to and preferably in contact with interior housing 150 to restrict flow into filament wells 140 and 150. Porous film 170 may comprise, for example, a thin section of porous polytetrafluoroethylene material such as a GORE-TEX® membrane having a thickness of approximately 0.010 in. and a porosity of approximately 68%.

Preferably, gas detection device 100 further comprises a filter to "scrub" environmental gases before such gases enter filament wells 140 and 150 to remove certain compositions therefrom which may detrimentally affect or poison pelements 120 and/or 130. Such a filter may be placed adjacent to and preferably in contact with porous film 170 and comprise part of the flow limiter.

As also illustrated in FIG. 2C, a flow director 180 is preferably located adjacent to and preferably in contact with porous film 170. Flow director 180 comprises a first passage 190 therethrough positioned in general alignment with filament well 140 in internal housing 160, to provide substantially direct or linear fluid connection between first passage 190 and filament well 140 through porous film 170. Flow director 180 also comprises a second passage 200 therethrough positioned in general alignment with filament well 150 in internal housing 160, to provide substantially direct fluid connection between second passage 200 and filament well 150 through porous film 170. Flow director 180 also comprises a channel 210 providing fluid connection between first passage 190 and second passage 200.

Flow inlet passage 320 is preferably positioned in general alignment with first passage 190 in flow director 180 to provide substantially direct or linear fluid connection between flow inlet passage 320 and first passage 190 through frit 220. Flow outlet passage 330 is preferably positioned in general alignment with second passage 200 in flow director 180 to provide substantially direct or linear fluid connection between flow outlet passage 330 and second passage 200 through frit 220.

Figure 2D:
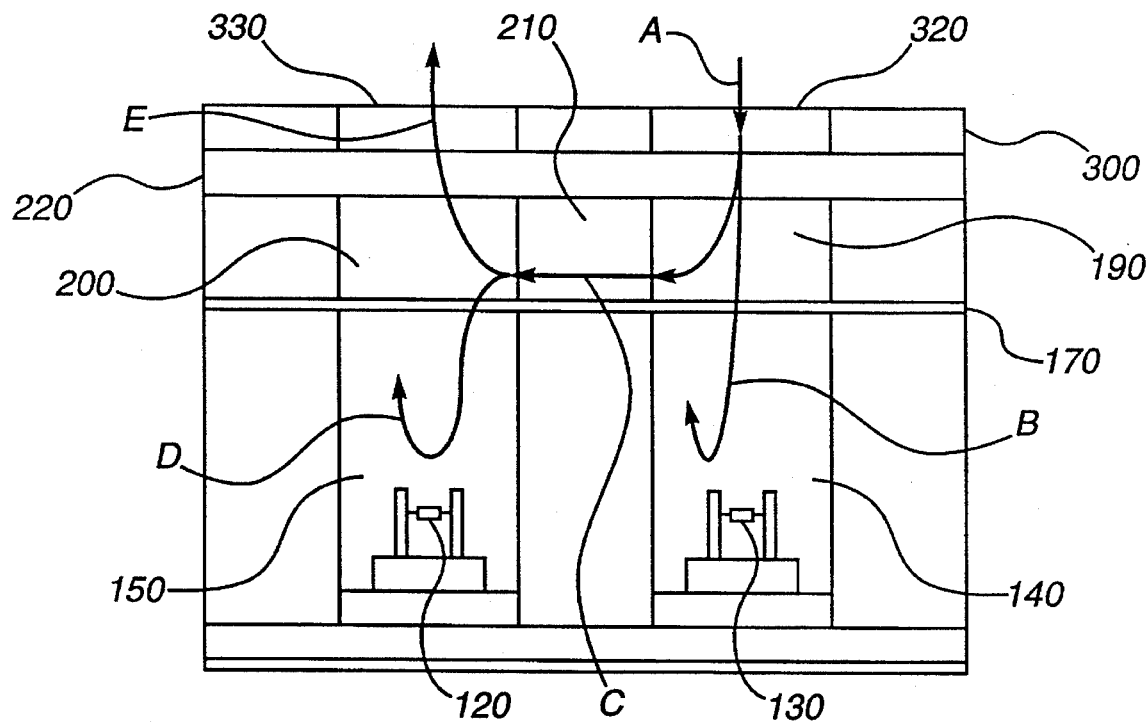
FIG. 2D illustrates in cross-section the embodiment of the present gas detection device set forth in FIG. 2C with arrows showing the flow of environmental gases therethrough.

The flow of environmental gases through gas detection device 100 of FIG. 2C is illustrated in FIG. 2D. As illustrated, an environmental gas stream A enters gas detection device 100 via flow inlet passage 320 and pass through frit 220 to first passage 190 in flow director 180. A portion B of the entering gas stream A passes through porous film 170 to circulate in first filament well 140 and contact compensating pelement 130. The flow of environmental gases preferably contacts compensating pelement 130 before contacting active pelement 120 to prevent the deposition of oxidized decomposition products upon compensating pelement 130.

Another portion C of the entering gas stream A passes through channel 210 in flow director 180 to second passage 200. A portion D of portion C of the gas stream A passes through porous medium 170 to circulate in second filament well 150 and contact active pelement 120. A portion E of portion C of the gas stream A exits gas detection device 100 through frit 220 and then outlet passage 330.

Figure 1A:
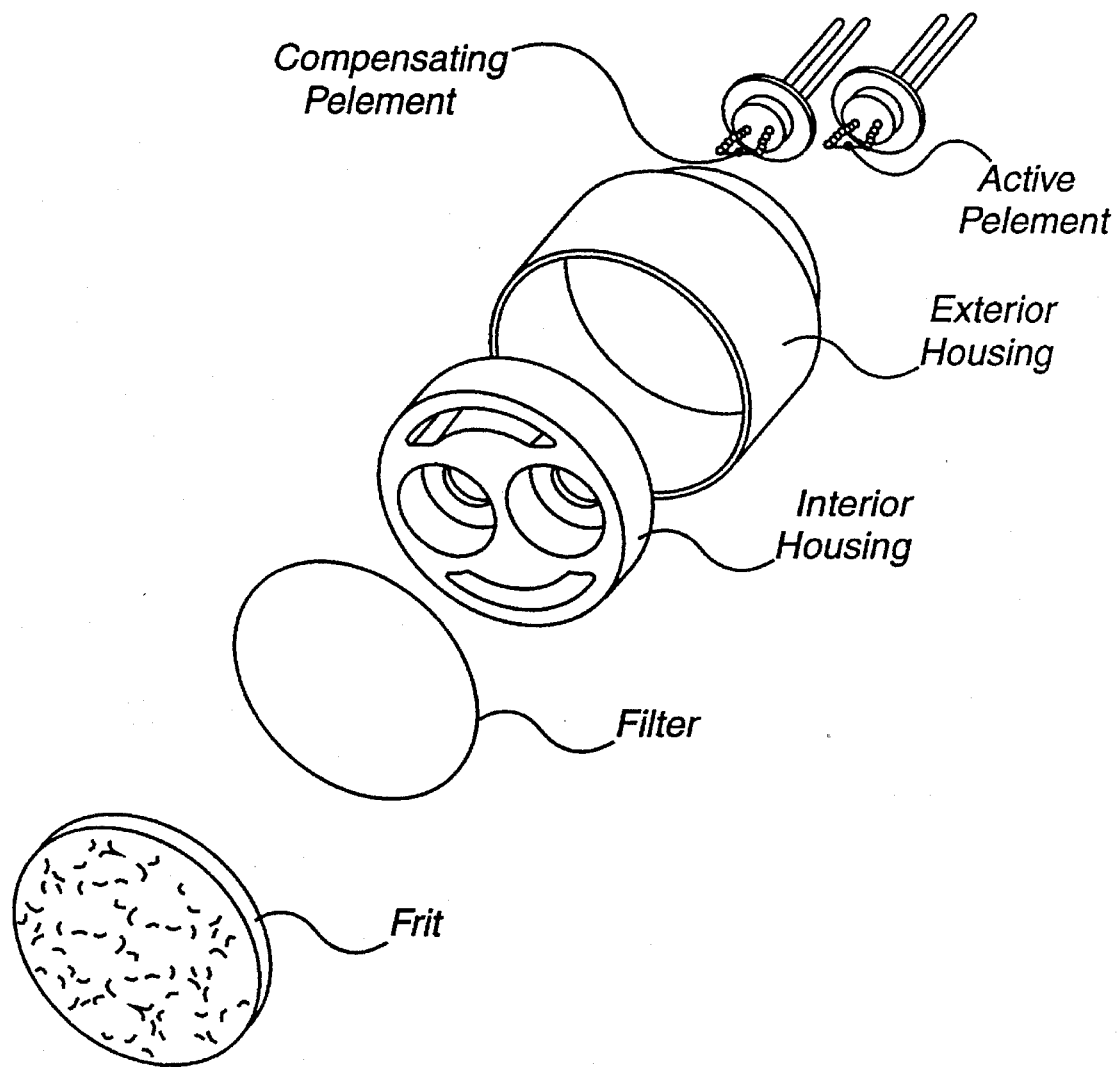
FIG. 1A illustrates an existing modular combustible gas detection unit which operates by diffusion.
Figure 1B:
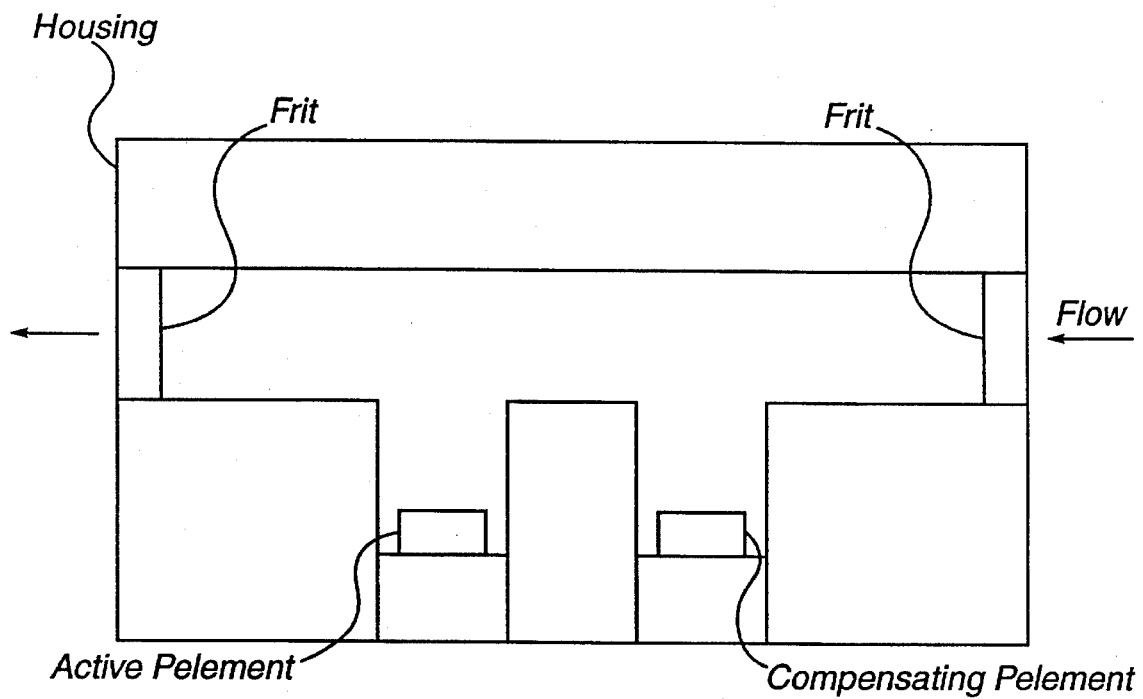
FIG. 1B illustrates an existing combustible gas detection unit which operates under forced flow of environmental gases therethrough.

By providing a substantially direct/linear forced flow (that is, forced flow parallel to the axes of filament wells 140 and 150) of environmental gas through inlet flow passage 320 of manifold 300, through frit 220 to first passage 190, and then through porous film 170 to filament well 140 and 150, the response time of gas detection device 100 is substantially minimized. Moreover, the design of gas detection device 100 enables simple retrofit of diffusion gas detectors as illustrated in FIG. 1A to provide for operation in a flow-through detection mode. Still further, unlike previous gas detection cells, gas detection device 100 is quite suitable for operation in either a substantially direct flow-through or in a diffusion mode.

Figure 4A:
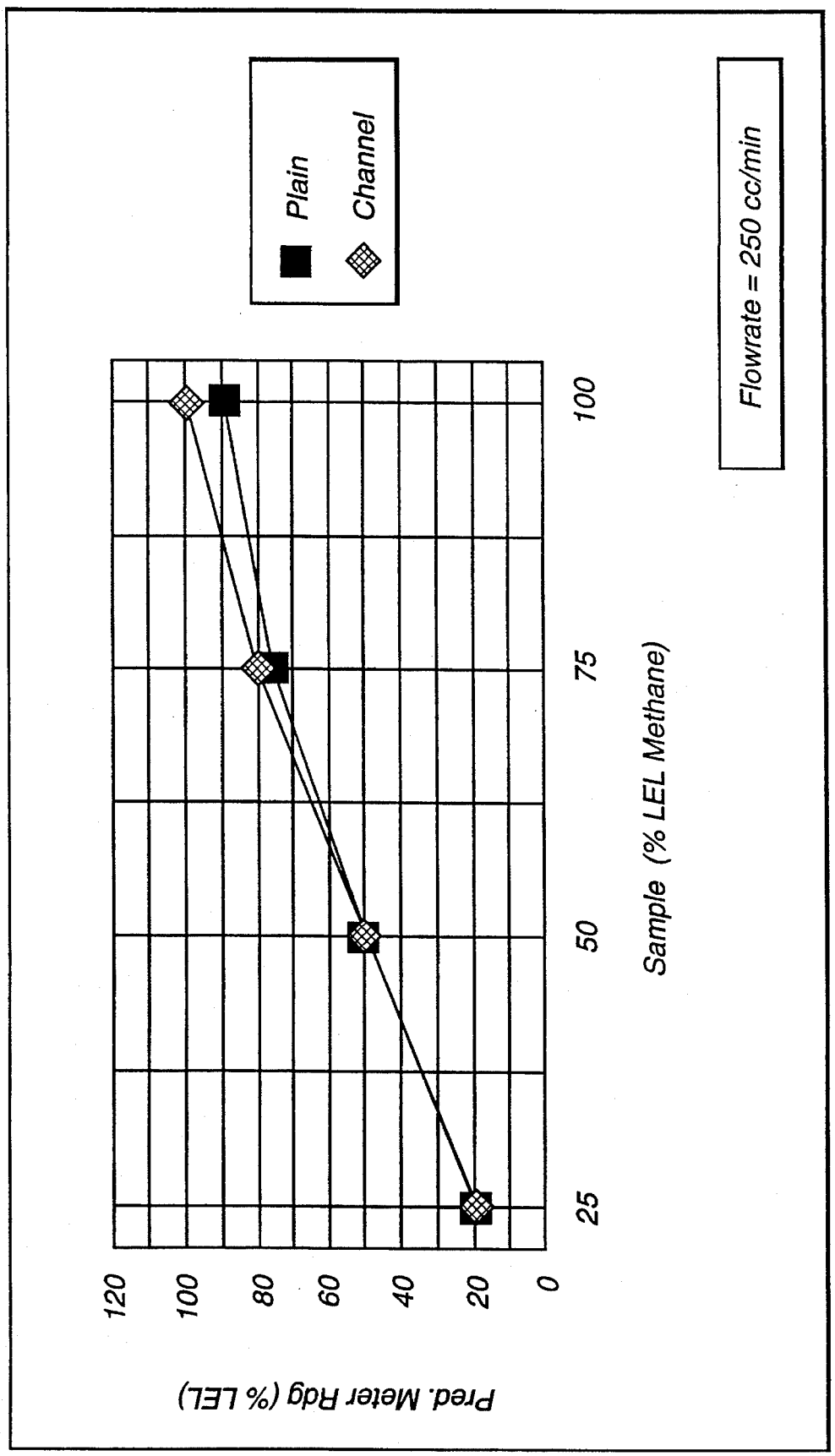
FIG. 4A illustrates the performance of the present device in the 0 to 100% LEL (Lower Explosion Limit) range for methane with and without (plain) a bypass channel in the manifold at a current of 135 mA.
Figure 4B:
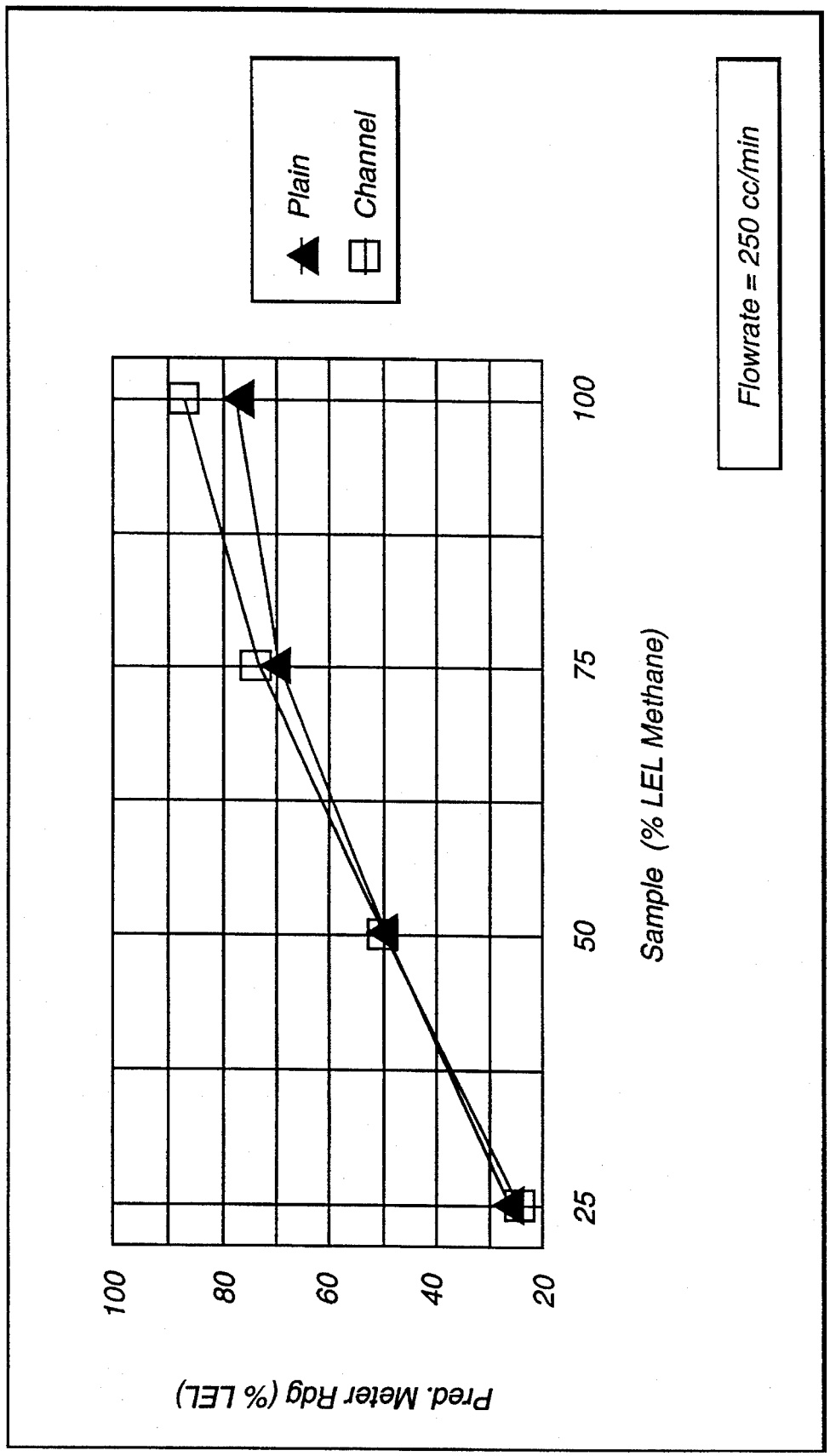
FIG. 4B illustrates the performance of the present device in the 0 to 100% LEL (Lower Explosion Limit) range for methane with and without (plain) a bypass channel in the manifold at a current of 130 mA.

FIGS. 4A and 4B set forth two studies of the effect of bypass channel 350 in the embodiment of gas detection device 100 illustrated in FIG. 2C over a concentration range of 0 to 100% LEL for methane. In these studies, a flow rate of approximately 250 cc/min to manifold 300 was utilized. To satisfy current regulatory standards, a combustible gas detector must be capable of distinguishing between concentration levels of ±5% over the entire range of concentrations to be detected. It is preferable, therefore, to maximize the difference in signal obtained between different concentration levels (that is, the slope of the idealized line drawn in FIGS. 4A and 4B is preferably maximized over the entire range of concentrations) to enable the distinction of such different concentration levels over noise levels.

Because active pelement 130 may become overwhelmed at a particular flow rate as concentration level of combustible gas in increased, the signal provided by gas detection device 100 at higher concentrations may be less than theoretically predicted. This phenomena is illustrated in FIGS. 4A and 4B by the reduction in the slope of the lines drawn thereon at higher concentrations. In both studies, inclusion of bypass channel 350 in manifold 300 improved the performance of gas detection device 100 at higher concentrations of methane.

Figure 4C:
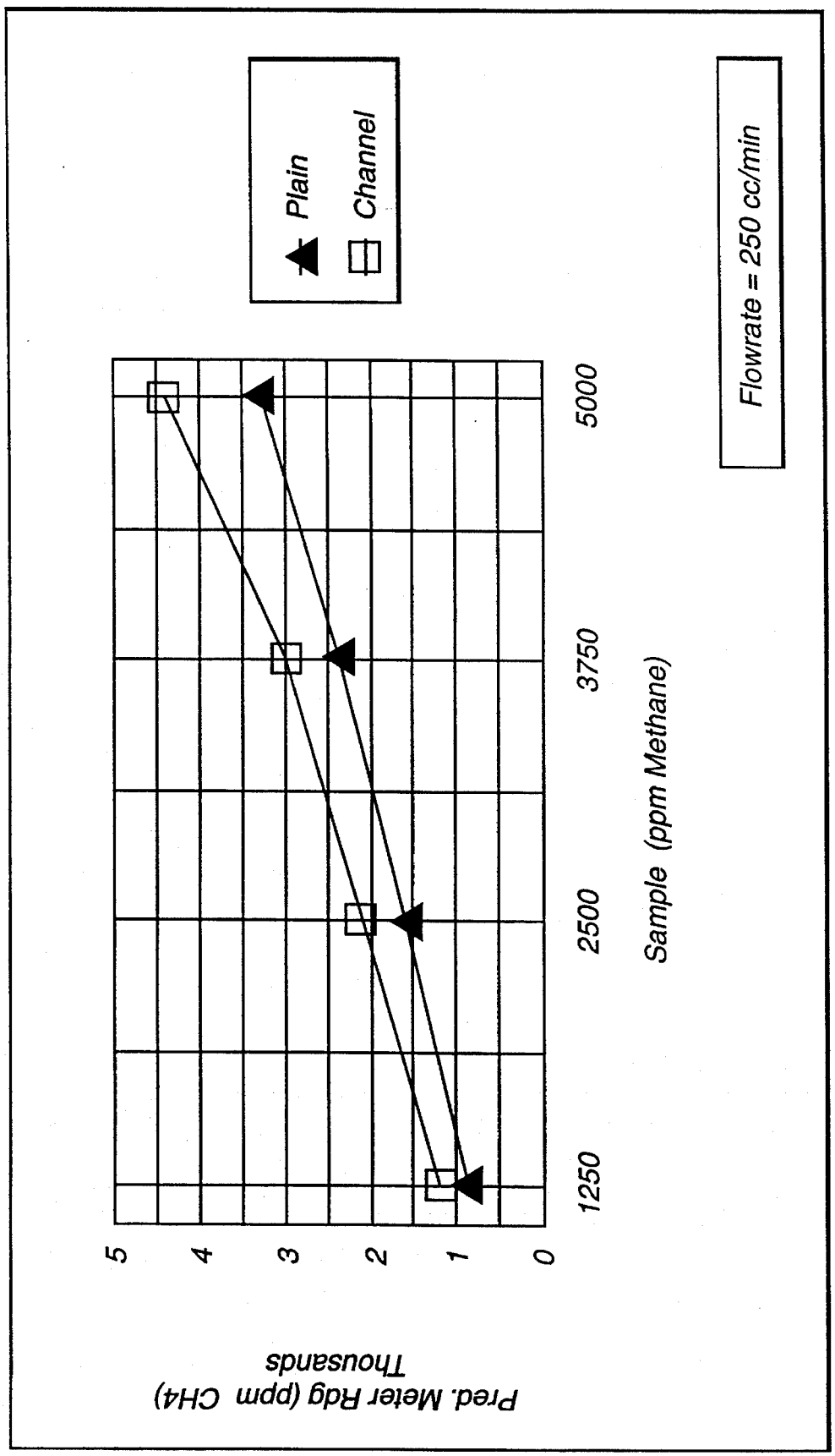
FIG. 4C illustrates the performance of the present device in the 0 to 5000 PPM range for methane with and without (plain) a bypass channel in the manifold at a current of 130 mA.
Figure 4D:
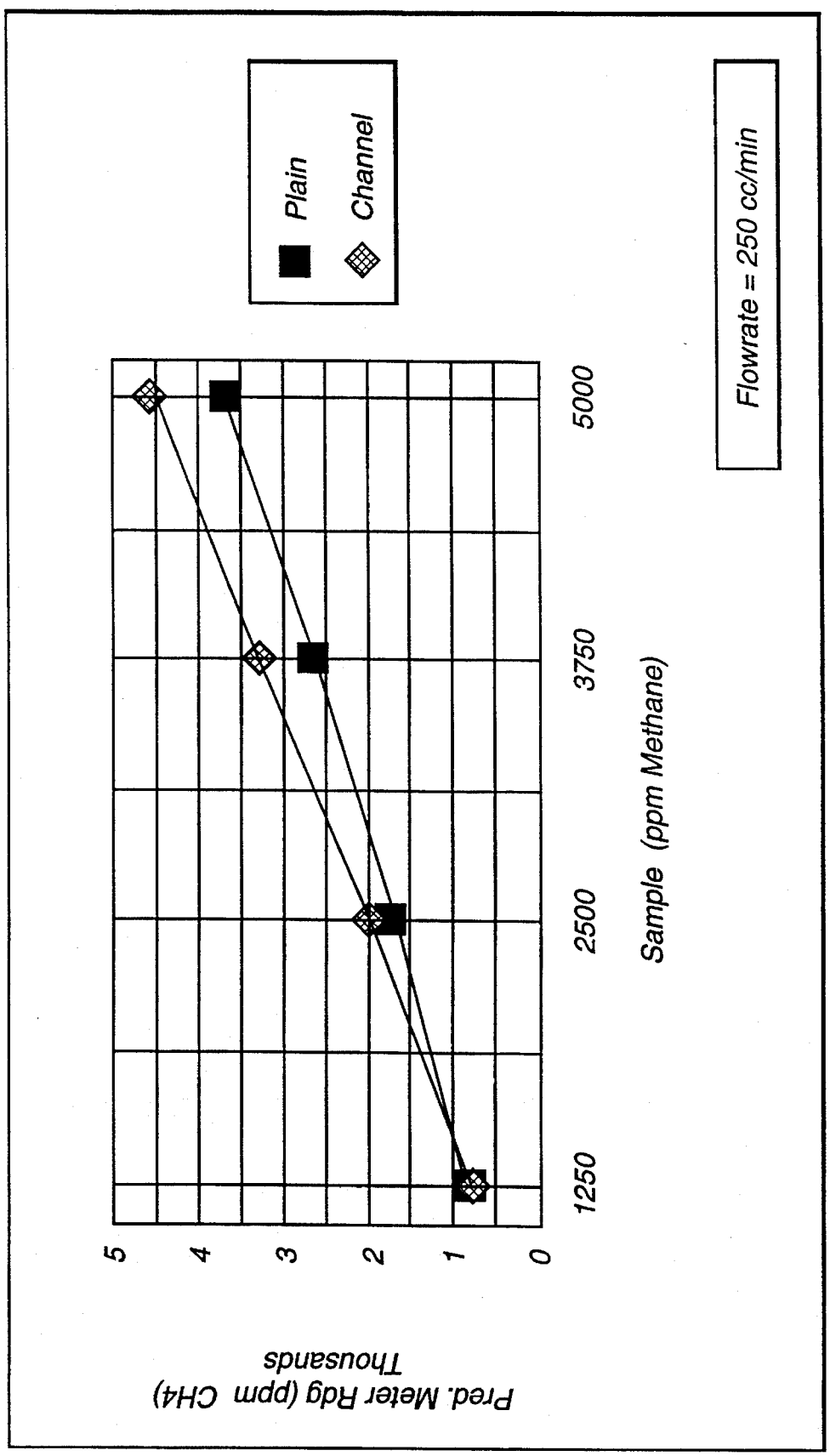
FIG. 4D illustrates the performance of the present device in the 0 to 5000 PPM range for methane with and without (plain) a bypass channel in the manifold at a current of 135 mA.

This effect is also illustrated in FIGS. 4C and 4D for gas detection device 100 as illustrated in FIG. 2C over a concentration range of approximately 1250 to 5000 PPM methane. The flow rate used in these studies was once again 250 cc/min.

Figure 4E:
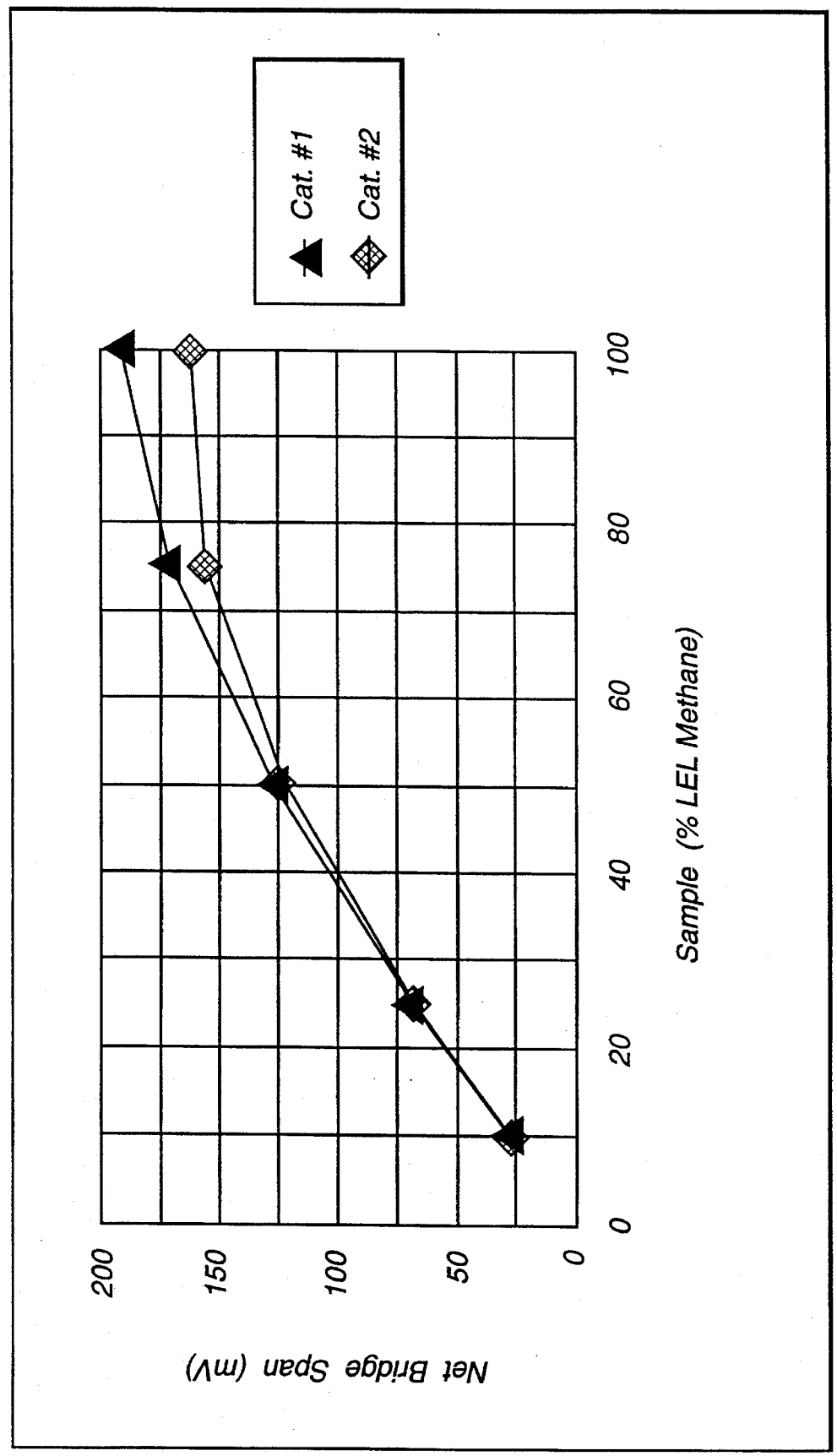
FIG. 4E illustrates the performance of the present device in the 10 to 100% LEL (Lower Explosion Limit) range for methane using pelements having different amounts of catalyst thereon.

By increasing the amount of catalyst present upon active pelement 130, the flux of combustible gas (that is, the forced flow rate of environmental gasses) into gas detection device can be increased while maintaining a distinguishable signal from the Wheatstone bridge between various gas concentrations. In other words, the gas concentration at which active pelement 130 is overwhelmed is increased by simply increasing the amount of catalyst upon active pelement 130. This effect is illustrated in FIG. 4E over a concentration range of approximately 10 to 100% LEL for methane. The gas detection device represented by Cat. #2 in FIG. 4E had more active catalyst present upon active pelement 120 than the gas detection device represented by Cat. #1.

In the experiments of FIG. 4E gas detection device 100 as illustrated in FIG. 2C was used with a flow rate of approximately 250 cc/min to manifold 300. The width of channel 350 of manifold 300 in the studies represented in FIG. 4E was approximately 0.040 in.

Figure 5A:
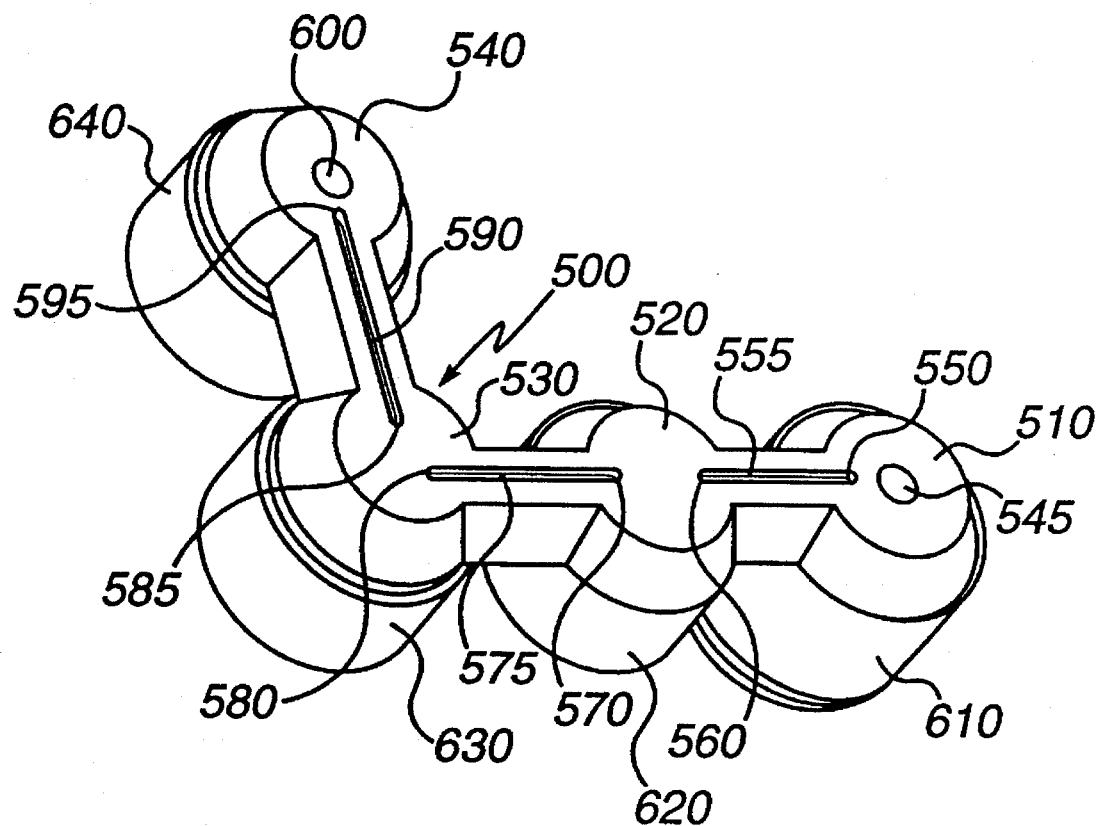
FIG. 5A illustrates a top perspective view of an embodiment of a manifold for use in a detector comprising multiple detection cells.
Figure 5B:
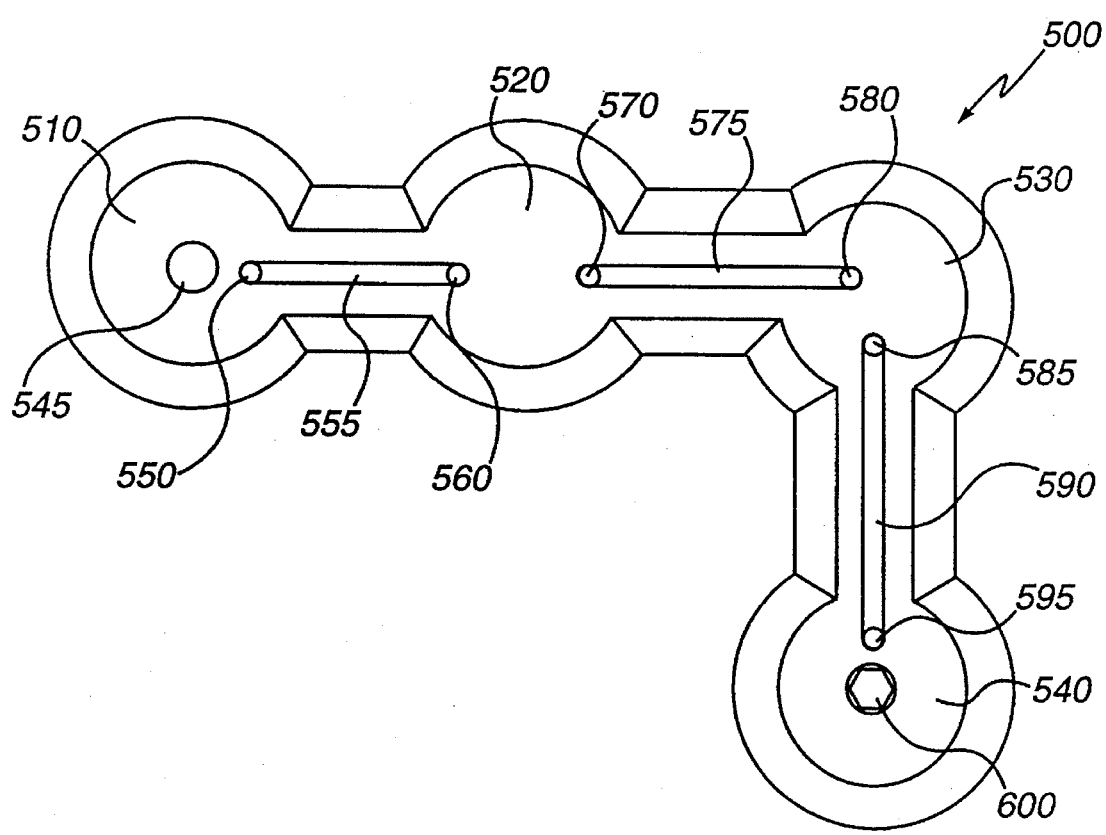
FIG. 5B illustrates a top plan view of the manifold of FIG. 5A.
Figure 5C:
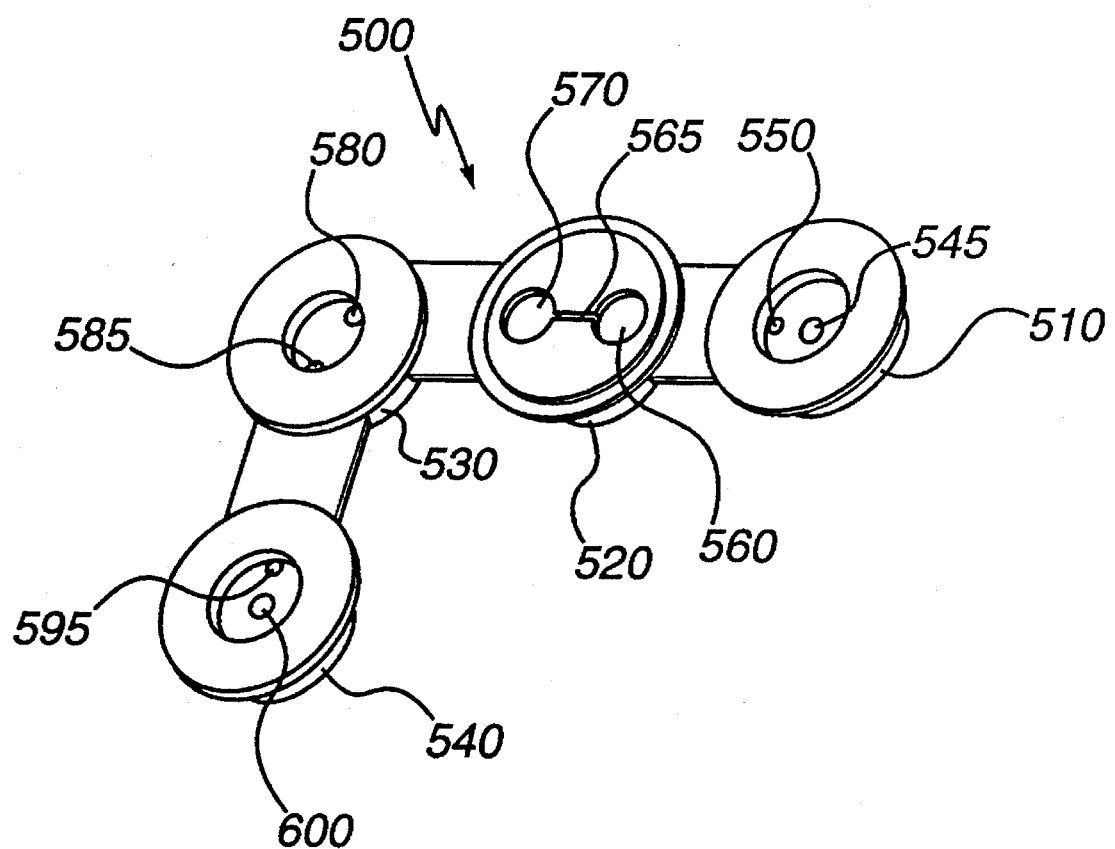
FIG. 5C illustrates a bottom perspective view of the manifold of FIG. 5A.

Gas detection device 100 is also well suited to incorporation into a multiple gas detection/monitoring unit by modification of the manifold. A manifold 500 for use in a multiple gas detection unit is illustrated in FIGS. 5A through 5C. As illustrated in FIGS. 5A through 5C, manifold 500 comprises a first manifold member 510, a second manifold member 520, a third manifold member 530 and a fourth manifold member 540. First manifold member 510, second manifold member 520, third manifold member 530 and fourth manifold member 540, are positioned to be seated adjacent to and preferably in substantially sealing contact with a first detection device 610, a second detection device 620, a third detection device 630 and a fourth detection device 640, respectively.

First manifold member 510 comprises and inlet passage 545 through which environmental gases enter and an outlet passage 550. Outlet passage 550 of first manifold member 510 is in fluid connection via channel 555 with an inlet passage 560 of second manifold member 520. Outlet passage 570 of second manifold member 520 is in fluid connection via channel 575 with inlet passage 580 of third manifold member 530. Outlet passage 585 of third manifold member 530 is in fluid connection via channel 590 with inlet passage 595 of fourth manifold member 540. The gas flow exits the system of detection devices 610, 620, 630 and 640 via outlet passage 600 of fourth manifold member 540.

First detection device 610, second detection device 620, third detection device 630 and fourth detection device 640 may respectively comprise, for example, an oxygen detector, a combustible gas detector, a first toxic gas detector and a second toxic gas detector. In the case that an oxygen detector is combined with a combustible gas detector, it is preferable to place the oxygen detector prior in the series of detectors to the combustible gas detector to ensure that the original oxygen concentration of the gas flow from the environment is maintained at the point of the oxygen detector. As illustrated in FIG. 5C, second manifold member (corresponding to combustible gas detection device 620) comprises a bypass channel 565 for providing fluid connection between inlet passage 560 and outlet passage 570.

Because of the diminution in the oxygen level above the 100% LEL range (approximately 5% concentration for methane), catalytic oxidation is not a suitable method for determining the concentration of combustible gases present in a particular environment. At such concentrations, thermal conductivity of the environmental gas is used to determine combustible gas concentration.

It is common to use an uncoated platinum wire in making such determinations. In practice, a constant current is transmitted through the platinum wire and the electrical resistance thereof is measured. Using methane as an example, as methane concentration increases, the thermal conductivity of the environmental gas increases and the temperature of the wire decreases. This decrease in temperature is reflected in the measured resistance of the platinum wire, thereby providing an indication of the methane content of the environmental gas.

Prior gas detectors designed to operate in the 0 to 100% LEL range as well as above the 100% LEL range, generally include both active and compensating pelements as illustrated in FIG. 1A (for use in the 0 to 100% LEL range) and an uncoated platinum wire (for use in the above 100% LEL range). To conserve power, when operating in the 0 to 100% LEL range, current is transmitted through the active and compensating pelements only. To operate in the above 100% LEL range, current to the active and compensating pelement is switched off (generally manually), while current to the platinum wire is switched on. A delay in operation is experienced while the platinum wire is allowed to reach operating temperature. A similar delay is experienced when returning to the 0 to 100% LEL range (that is, upon once again supplying current to the active and compensating pelements).

Applicants have discovered that the requirement of a separate platinum wire can be eliminated by using compensating pelement 130 to measure the thermal conductivity of the environmental gas in the above 100% LEL range. Thus, the change in the electrical resistance of the compensating pelement is measured as a function of combustible gas concentration. The delay associated with heating a separate platinum element to operating temperature is thereby eliminated.

Applicants have also discovered that it is preferable to reduce the temperature of the active pelement below a temperature at which substantial catalytic oxidation occurs when operating in concentration ranges above 100% LEL. At such concentrations, it is found that if the active pelement is maintained above a temperature at which substantial catalytic oxidation occurs the signal from the Wheatstone bridge circuit does not return to the calibrated zero point when the combustible gas concentration is reduced to zero for several minutes thereafter. Erroneous gas concentrations as high as 10% may be given for several minutes after the combustible gas concentration is reduced to zero. It is believed that this phenomena is a result of "coking" occurring upon the active pelement. After several minutes, the signal is found to reduce to zero. It is believed that residual or coke products are "burned off" the active pelement during this time. Clearly, however, the gas detection device will not properly operate to determine gas concentrations in the 0 to 100% LEL and PPM ranges during this time.

Figure 6:
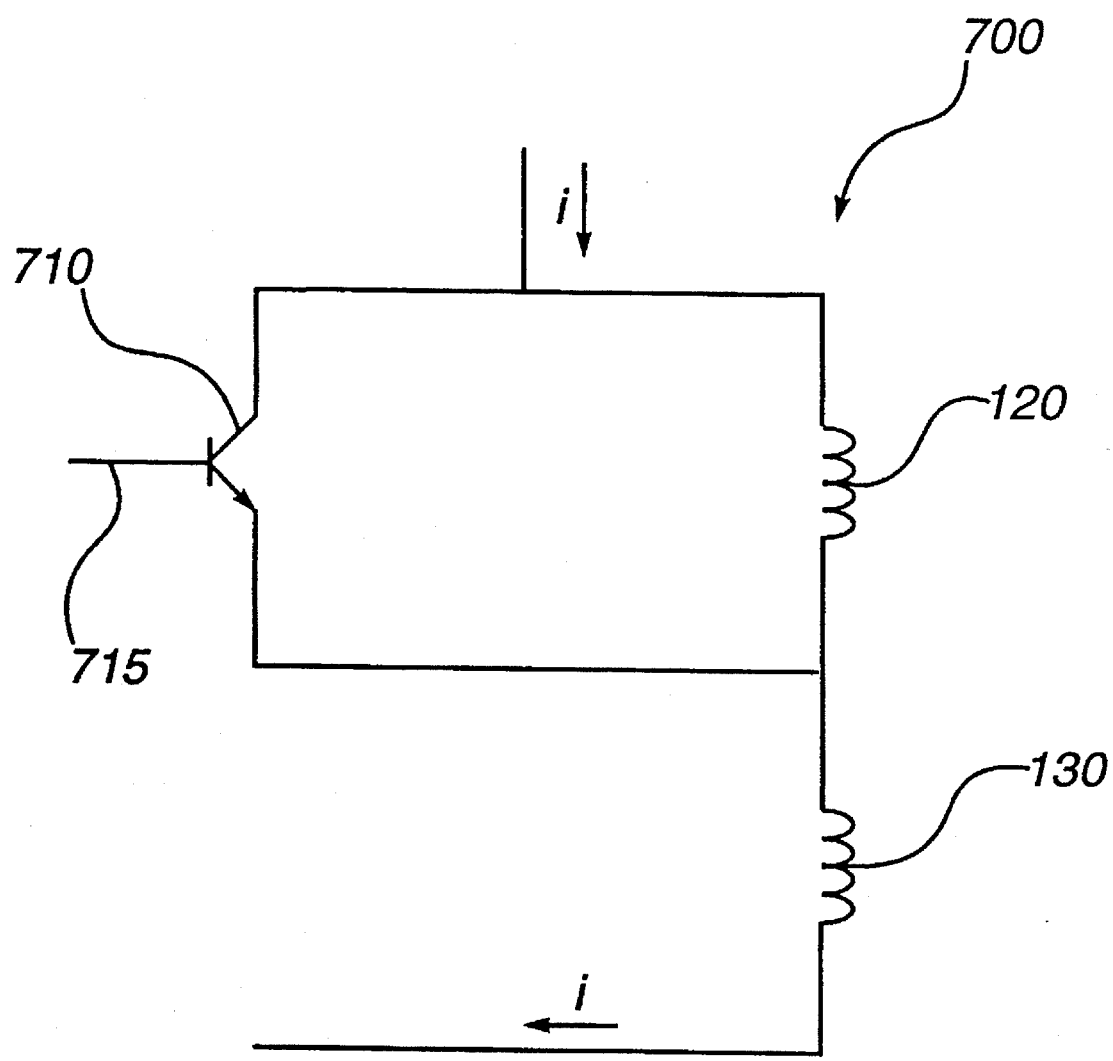
FIG. 6 illustrates the use of an electrical shunt around the active pelement to decrease the current through the active pelement during operation in concentration ranges above 100% LEL.

By reducing the current through active pelement 130 such that the temperature of active pelement 130 is reduced to a temperature at which insubstantial catalytic oxidation occurs, the above-described coking phenomena is minimized or eliminated. This result may easily be accomplished by providing an electrical "shunt" around active pelement 120 as illustrated in FIG. 6. As known in the art, the temperature below which catalytic oxidation substantially ceases depends upon the combustible gas being oxidized and the identity of the catalyst.

As shown in FIG. 6, a transistor 710 is preferably included in circuit 700. In all other respects, the circuit used in gas detection device 100 is the commonly used Wheatstone bridge circuit. In operation of gas detection device 100 in the PPM and 0 to 100% LEL ranges, a constant current i is transmitted through active pelement 120 and compensating pelement 130. During such operation, substantially no current is transmitted through transistor 710. In the 0 to 100 LEL range, transistor 710 is thus maintained in a low-conductivity state.

In the operation of gas detection device in the above 100% LEL range, transistor 710 is "switched on" to a high-conductivity state by applying a voltage to base 715 of transistor 710. In the high conductivity state, transistor 710 acts like a low-resistance resistor and a portion of current i is transmitted therethrough. The current transmitted through active pelement 120 is thereby reduced while the current transmitted through compensating pelement 130 remains substantially unchanged.

The resistance of transistor 710 may be selected to draw as much current as desired to create a corresponding temperature reduction in active pelement 120. In one experiment using an active pelement 120 with a resistance of approximately 7 ohm, a transistor having a resistance of approximately 2 ohm when in the high-conductivity state was successfully used to reduce the temperature of active pelement 120 when operating in the above 100% LEL range. Using current i of approximately 130 mA, for example, the voltage drop across active pelement 120 was reduced from approximately 1 V to approximately 0.2 V upon switching (2-ohm) transducer 710 to the high-conductivity state. Catalytic oxidation of methane was substantially eliminated when transducer 710 was in the high-conductivity state. In this experiment, no coking phenomena was observed in operation in concentrations of methane above 100% LEL.

Although, the present invention has been described in detail in connection with the above examples, it is to be understood that such detail is solely for that purpose and that variations can be made by those skilled in the art without departing from the spirit of the invention except as it may be limited by the following claims.

What is claimed is:

1. A gas detection device for the detection of combustible gases in a surrounding environment comprising, an exterior housing, an active pelement disposed within the exterior housing and a compensating pelement disposed within the exterior housing, the gas detection device further comprising a porous frit seated within a distal end of the exterior housing to separate the active pelement and the compensating pelement from the surrounding environment, the porous frit adapted to prevent flashback into the surrounding environment while allowing entry of environmental gas through the porous frit to contact the active pelement and the compensating pelement, the porous frit having an interior side within the exterior housing and an exterior side outside the exterior housing, the gas detection device further comprising a flow guide for directing flow of environmental gas into the gas detection device disposed adjacent the exterior side of the porous frit, the flow guide comprising an inlet port through which a forced flow of environmental gas is directed by an external pump to pass through the porous frit and into the exterior housing in a direction generally parallel to the axis of the exterior housing to contact the active pelement and the compensating pelement, the flow guide further comprising an outlet port through which gas may exit the exterior housing.

2. The gas detection device of claim 1 wherein the flow guide further comprises a bypass passage for allowing a portion of environmental gas pumped to the inlet port to bypass the porous frit in a flow controlling function that never permits said portion of environmental gas to enter within the exterior housing.

3. The gas detection device of claim 2 wherein the bypass passage comprises a channel providing fluid connection between the inlet port and the outlet port.

4. The gas detection device of claim 2 further comprising an interior housing, the interior housing comprising a first filament well therein in which the compensating pelement is disposed and a second filament well therein in which the active pelement is disposed, the interior housing further comprising a passage for providing fluid connection between the first filament well and the second filament well.

5. The gas detection device of claim 2 further comprising an interior housing, the interior housing comprising a first filament well therein in which the compensating pelement is disposed and a second filament well therein in which the active pelement is disposed, the gas detection device further comprising a porous membrane disposed adjacent the interior housing, the gas detection device further comprising a flow director disposed adjacent the porous membrane, the flow director comprising a first passage therethrough, the first passage being in generally linear alignment with the first well to provide substantially direct fluid contact with the first well through the porous film, the flow director also comprising a second passage therethrough, the second passage being in generally linear alignment with the second well to provide substantially direct fluid contact with the second well through the porous film, the flow director further comprising a passage therein for providing fluid connection between the first passage and the second passage, the inlet port being in generally linear alignment with the first passage in the flow director to provide substantially direct fluid connection between the inlet port and the first passage through the porous frit, the outlet port being in generally linear alignment with the second passage in the flow director to provide substantially direct fluid connection between the outlet port and the second passage in the flow director through the porous frit.

6. The gas detection device of claim 5 wherein the porous film is fabricated of a polytetrafluoroethylene material.

7. The gas detection device of claim 6 further comprising a filter to remove certain contaminants from environmental gas flowing therethrough to prevent detrimental effects of such contaminants.

8. The gas detection device of claim 1 wherein the electrical resistance of the compensating pelement is used to determine concentration of combustible gas above a predetermined combustible gas concentration level.

9. The gas detection device of claim 8 further comprising a circuit for reducing current passing through the active pelement, thereby reducing the temperature of the active pelement below a temperature at which substantial catalytic oxidation occurs, when the gas detection device is being used in an environment where the level of combustible gas is above the predetermined concentration level of combustible gas.

10. The gas detection device of claim 9 wherein the circuit for reducing current passing through the active pelement comprises a transistor in parallel electrical connection with the active pelement, the transistor adapted to be switchable between a high-conductivity state and a low-conductivity state.

11. A gas detection device comprising an active pelement, a compensating pelement and a circuit for measuring the electrical resistance of the compensating pelement, wherein the electrical resistance of the compensating pelement is used to determine concentration of combustible gas at combustible gas concentration levels above a 100% LEL (Lower Explosive Limit).

12. The gas detection device of claim 11 further comprising a circuit for reducing current passing through the active pelement, thereby reducing the temperature of the active pelement below a temperature at which substantial catalytic oxidation occurs, when the gas detection device is being used above the predetermined concentration level.

13. The gas detection device of claim 12 wherein the circuit for reducing current passing through the active pelement comprises a transistor in parallel electrical connection with the active pelement, the transistor adapted to be switchable between a high-conductivity state and a low-conductivity state.

* * * * *